United States Patent
Woodard et al.

[11] Patent Number: 6,102,845
[45] Date of Patent: Aug. 15, 2000

[54] VENTRICULAR ASSIST DEVICE WITH MINIMAL BLOOD CONTACTING SURFACES

[75] Inventors: John C. Woodard, Walnut Creek; Ronald A. Ness, Castro Valley; Richard M. Romley, Alameda; Than Nguyen, Huntington Beach; Herbert Chen, Kensington, all of Calif.

[73] Assignee: Baxter International Inc., Deerfield, Ill.

[21] Appl. No.: 08/192,894

[22] Filed: Feb. 7, 1994

[51] Int. Cl.[7] .......................................... A61M 1/12
[52] U.S. Cl. ..................................... 600/16; 623/3; 623/2
[58] Field of Search .................... 623/3, 2, 900; 600/16; 606/153

[56] References Cited

U.S. PATENT DOCUMENTS

| | | | |
|---|---|---|---|
| 3,409,914 | 11/1968 | Jones | 623/3 |
| 4,086,665 | 5/1978 | Poirier . | |
| 4,195,623 | 4/1980 | Zeff et al. . | |
| 4,222,127 | 9/1980 | Donachy et al. . | |
| 4,247,292 | 1/1981 | Angell | 8/94.11 |
| 4,581,029 | 4/1986 | Joh . | |
| 4,629,459 | 12/1986 | Ionescu et al. | 623/2 |
| 4,650,486 | 3/1987 | Chareire | 606/153 X |
| 4,759,758 | 7/1988 | Gabbay | 623/2 |
| 4,759,759 | 7/1988 | Walker et al. | 623/2 |
| 4,781,716 | 11/1988 | Richelsoph | 623/3 |
| 4,838,889 | 6/1989 | Kolff | 623/3 |
| 4,902,291 | 2/1990 | Kolff | 623/3 |
| 4,925,377 | 5/1990 | Inacio et al. | 417/472 |
| 5,123,919 | 6/1992 | Sauter et al. | 623/2 |
| 5,129,789 | 7/1992 | Thronton et al. | 417/53 |
| 5,133,744 | 7/1992 | Ramos Martinez . | |
| 5,139,515 | 8/1992 | Robiczek | 623/1 |
| 5,147,385 | 9/1992 | Beck et al. | 623/1 |

FOREIGN PATENT DOCUMENTS

| | | |
|---|---|---|
| 0 170 262 | 2/1986 | European Pat. Off. . |
| 2619239 | 7/1977 | Germany . |
| 1 268 484 | 3/1972 | United Kingdom . |
| 1 315 844 | 5/1973 | United Kingdom . |
| 1 315 845 | 5/1973 | United Kingdom . |
| 1 477 643 | 6/1977 | United Kingdom . |
| 2 187 535A | 9/1987 | United Kingdom . |
| WO 90/14804 | 12/1990 | WIPO . |
| WO 93/20757 | 10/1993 | WIPO . |

*Primary Examiner*—David H. Willse
*Attorney, Agent, or Firm*—Oppenheimer Wolff & Donnelly; Bruce Canter; Guy Cumberbatch

[57] ABSTRACT

A ventricular assist device includes a pair of valved conduits and a pumping portion connected by these conduits into the circulatory system of a host patient. The pumping portion and valved conduits are constructed and configured to minimize the number of material-surface transitions which blood must cross in flowing through the device. Also, the valved conduits include porcine xenograft valves, which are externally supported by stenting structure located outside of the blood-contacting flow path of the device. A flexible shape-retaining inner wall member of the valved conduits is impervious to blood, but defines a porous inner surface on which a stable biological interface may form. Also, this inner wall member is shaped with sinuses which do not replicate either the porcine sinuses from which the xenograft valves were taken, or human aortic sinuses. However, the sinuses of the inner wall member are configured to provide effective valve action by the formation of vigorous vortices in the blood flow downstream of these valves, and to avoid the formation of clots on the blood-contacting surfaces of the valved conduits.

40 Claims, 7 Drawing Sheets

VENTRICULAR ASSIST DEVICE WITH MINIMAL BLOOD CONTACTING SURFACES

BACKGROUND OF THE INVENTION

1. Field of the Invention

The present invention is in the field of ventricular assist devices, and of artificial prosthetic conduits used for transporting blood in the circulatory system of a living organism. More particularly, the present invention relates to a ventricular assist device which includes a continuous unitary blood-contacting membrane defining a variable-volume cavity, expansion and contraction of which is effective to pump blood; and to a valved blood conduit for communicating blood to or from the variable-volume chamber, and having liquid-impermeable membrane or inner wall defining a blood-contacting surface within the conduit. The inner wall of the conduit sealingly engages the unitary blood-contacting membrane of the variable-volume chamber without a blood-contacting gasket or sealing member, so that only a single material-surface transition is experienced by the flowing blood upon entry into or outflow from the ventricular assist device.

Also, the present invention relates to an artificial conduit having therein a prosthetic bio-material valve structure, and associated conduit structure for ensuring a substantially laminar central jet of blood flow through the conduit and valve structure, while also ensuring that flow disruption is minimized, and that no blood stagnation or stasis volumes are formed downstream of or behind the valve structure. Still more particularly, the present invention relates to such a valved blood conduit having woven and/or knitted filamentary fabric walls which are impregnated outwardly with a biologically-compatible impermeable material so that the conduit walls are impermeable to blood, while the inner surface of the conduit wall remains textured or porous to promote the growth of a stable biological interface. Provision is made for sealingly connecting the valved blood conduit to other blood-carrying components without disruption of smooth and stasis-free blood flow. The connecting provisions also minimize the number of blood-contacting material-surface transitions, and provide for accommodation without loss of sealing integrity of dimensional changes which will occur at the connections after implantation of the valved conduit and assist device. These dimensional changes will occur as a transitional collagen or other bio-degradable coating of the conduit is absorbed, as components of the valved conduit and adjacent structure take a set with the passage of time after surgical implantation, and as a biological interface is formed on the blood-contacting surfaces by the host's circulatory system.

2. Related Technology

Ventricular assist devices have become increasingly recognized as potentially able to allow patient's whose natural heart is diseased or has been injured by trauma or heart attack, to recover and continue life, either while their natural heart heals, while awaiting a heart transplant, or even on a long-term basis with the extended aid of the ventricular assist device.

Particularly, left-ventricular assist devices (LVAD) are recognized as potentially very valuable for assisting patients who suffer from congestive heart failure. More than two and one-half million Americans suffer from congestive heart failure. Recently, a National Institutes of Health study estimated that as many as thirty-five thousand people could be candidates for use of a left-ventricular assist device. At present, the conventional ventricular assist devices are used for patients who are waiting for a heart transplant (a so-called, "bridge to transplant"), for patients whose natural heart is of such poor condition that the patient cannot be removed from a heart-lung machine without providing some assistance to the patient's heart following otherwise successful open-heart surgery, and for patients suffering from massive heart attacks that lead to circulatory collapse. The conventional left-ventricular assist devices are not generally considered to be viable candidates for long-term utilization outside of the clinical environment for a plurality of reasons.

Most heart disease involves the left ventricle of the heart. This pumping chamber is generally known as the workhorse of the heart. A patient with a non-functioning right ventricle can survive quite successfully provided that their pulmonary blood flow resistance is low enough to allow circulation through the lunge; and the rest of the body entirely as a result of the efforts of the left ventricle. However, collapse of the left ventricle is most often fatal. An LVAD is able to fully take over the function of this ventricle, thus perfusing the body with oxygen-rich blood. The LVAD attaches to the patient's natural heart, and to a natural artery, and can be removed if the natural heart recovers.

Blood flow in the LVAD is effected by expansion and contraction of a variable-volume chamber. One-way valves associated with the inflow and outflow ports of the LVAD provide for blood flow into the variable-volume chamber during expansion, and for blood flow out of this chamber, usually to the ascending thoracic aorta. These one-way flow valves may be constructed as part of the LVAD itself, or may be disposed in the blood-flow conduits which connect the LVAD to the heart and aorta. A pair of conduits respectively connect the inlet port of the assist V device to the left ventricle and the outlet port to the major artery which is to receive the blood flow from the device.

As described above, artificial blood conduits have become a valuable tool of modern medicine. One use of such artificial blood conduits is as a temporary or permanent prosthetic artery. Another use is in the connection of temporary blood pumps, or ventricular assist devices, between the left ventricle of the heart and a major artery. In such a use, the demands on the artificial blood conduit are great. The artificial conduit must deal with the pulsatile blood flow created by the host's own heart, as well as with the flow, pressure, and pulsations created by the assist device. The artificial conduit must function within or outside of the host patient's body, and not introduces or allow the entry of bacterial or other contamination into the host's body or circulatory system. Also, the artificial conduit must be connected to both the heart, or to a major artery of the host's circulatory system in order to allow connection of both the artificial conduit, and also of the ventricular assist device or pump.

A persistent problem with artificial blood conduits has been the provision of a valving device of the one-way type in these conduits so that a ventricular assist device can achieve pulsatile blood flow in response to the expansion and contractions of a variable-volume chamber of the assist device.

A conventional artificial blood conduit is know in accord with U.S. Pat. No. 4,086,665, issued May 2, 1978, to Poirier. The blood conduit of the Poirier patent is believed to include an internal convoluted fabric tube of essentially circular cylindrical configuration throughout its length. This inner fabric tube is carried within an outer tube, which is also convoluted over part of its length. The inner tube is porous while the outer tube is liquid impervious. A tri-foliate valving structure is provided in the conduit to ensure unidirectional blood flow in the conduit. This tri-foliate valving structure is taught by the Poirier patent to be a porcine xenograft, sutured into the fabric of the inner tube. A circular support ring may be disposed outside of the inner tube wall to assist in support of the xenograft. Provision is made for connection of the artificial blood conduit of Poirier to other blood-carrying structure, and to the vascular tissue or heart tissue of the host via suture rings. Essentially, Poirier teaches that the valved conduit may be connected to other blood-carrying structure by means of flanged connections using gasket-sealed interfaces and threaded collars which engage onto threaded portions of the adjacent conduit or other blood-carrying structure.

With the artificial blood conduit taught by the Poirier patent, the conduit structure itself is quite bulky, being composed of several concentric structures or elements, some of which are spaced apart radially from one another. As a result, the Poirier conduit has a considerable wall thickness built up by all of these individual wall elements. Additionally, the inner lumen or passageway of this artificial conduit does not provide for elimination of blood flow stagnation or stasis downstream of the tri-foliate valve structure. Accordingly, the stagnant blood may clot or may adhere to the walls of the conduit, to be shed eventually as emboli in the circulatory system of the host. Also, the annular space between the inner porous conduit and the outer impervious conduit may harbor bacterial contamination, and provide a site for bacterial growth and infection which is hidden from the patient's immune system.

A conventional bio-material xenograft valve is known in accord with U.S. Pat. No. 4,247,292, issued Jan. 27, 1981, to W. W. Angell. The Angell patent is believed to disclose an externally-stented natural tissue valve for heart implantation in which the natural xenograft tissue is sutured to a fabric covered plastic stent. The valve is secured into a patient's heart by sutures between the suture ring and the heart tissue. There is no artificial conduit which is valved by the device of Angell.

Another conventional artificial conduit is disclosed by U.S. Pat. No. 5,139,515, issued Aug. 18, 1992 to F. Robicsek. The Robicsek patent is believed to disclose an artificial aortic root portion which includes a convoluted wall formed with sinuses generally aligned with the leaflets of the natural tri-foliate valve of the patient's heart. As so configured, it is asserted that the blood flow "recoil" downstream of the valve leaflets will assist in their closing, resulting in a more natural valve function, with reduced regurgitaition. However, the artificial aortic root portion taught by Robicsek includes out-pouchings, or sinuses, which are themselves formed with corrugations or convolutions like the rest of the artificial conduit. These convolutions at the sinuses themselves may contribute to the formation of small localized turbulent zones, or to the formation of stasis or stagnation volumes where blood flow is slowed or stopped. In either case, the fluid flow dynamics of the artificial conduit suggested by the Robicsek patent is highly questionable because it may cause the formation of clots which are eventually shed as emboli in the circulatory system.

Yet another artificial valve is known in accord with British patent specification No. 1315845, of B. J. Bellhouse, the complete specification for which was published on May 2, 1973. The Bellhouse specification is believed to disclose an artificial valve for implantation within the natural aortic root, with a ring part formed of silicone-coated uncut polyethylene terephthalate fabric. The cusps of this valve are formed of woven and/or knitted material of the same type of polyethylene terephthalate fabric, which is also coated with silicone rubber. However, the valve of Bellhouse is implanted into the natural aortic root, with the natural sinuses present, and does not include a prosthetic conduit for blood flow.

A persistent problem with all of the above-identified conventional devices, and with others which are known also in the art, is the rather high number of material-surface transitions, or changes in the material across which the patient's blood must flow in passing through the devices. For example, in the artificial blood conduit of Poirier, disclosed in the '665 patent, the flowing blood is exposed to at least nine different surfaces in flowing through this device. These different surfaces include the tissue surfaces of the porcine xenograft, the sutures which secure this graft, the fabric inner conduit, the gasket surfaces at the ends of the valved conduit, and the end connectors to which the fabric inner conduit connects. When the entire ventricular assist device of Poirier is considered, several additional blood-contacting surfaces of different materials, or material-surface transitions, must also be added to this list. Each of these blood-contacting material-surface transitions represents a potential source of turbulence in the flowing blood if the adjacent surfaces do not align perfectly with one another.

Additionally, the flowing blood may not have the same affinity for creating a stable biological interface with each of the various materials. That is, the material surfaces may have a differing degrees of surface porosity, of surface roughness, of surface energy, or of bio-compatibility with the host, for example. Consequently, with the passage of time, the biological interface between the flowing blood and the artificial, "not self" surfaces will be laid down with discontinuities, or with changes in tenacity of attachment to the underlying artificial surfaces, for example, at these material-surface transitions in the device. Each of these discontinuities or changes in tenacity of attachment of the biological interface with the underlying artificial structure represents an opportunity for a portion of the interface to slough off to become an emboli in the circulating blood. Also, blood may clot at these unstable interfaces, also representing a risk of forming emboli in the blood.

SUMMARY OF THE INVENTION

In view of the deficiencies of the conventional related technology outlined above, it is an object for this invention to provide a ventricular assist device having a variable-volume chamber, and a pair of valved conduits connecting the variable-volume chamber to the circulatory system of a patient, and in which the number of blood-contacting material-surface transitions is minimized.

More particularly, the present invention has as an object the provision of a ventricular assist device in which the variable-volume pumping chamber is formed of a single unitary blood-contacting flexible wall member, and this wall member is sealingly contacted by the material defining the blood-contacting wall of the valved conduit itself, without the use of gaskets or other sealing devices which are exposed to the flowing blood.

Still further to the above, the present invention has as an object the provision of a valved conduit in which the flowing blood is exposed only to the surfaces of a prosthetic valve, such as a porcine xenograft valve, to the sutures which secure this valve, and to the inner porous surface of a fabric conduit communicating the patient's circulatory system with the variable-volume chamber of the assist device.

Additionally, a further object of the present invention is to provide such a ventricular assist device, and valved conduit for such a device in which the fabric which defines the inner blood-contacting surface of the valved conduit is internally porous, but is impermeable to blood. Consequently, the fabric of this conduit presents a very favorable surface upon which a stable biological interface may be laid down by the flowing blood. On the other hand, this impervious fabric does not require an outer impervious conduit or tube like that used in the Poirier '665 patent in order to prevent blood from seeping through the fabric. This impervious fabric conduit can then be disposed in a perforate cage or support structure which is outwardly exposed to body fluids. Because the cage and fabric conduit are outwardly exposed to body fluids they do not provide a cavity or void in which a bacterial infection may be hidden from the immune system, as may occur with the device taught by the Poirier '665 patent.

Still further, an object of the present invention is to provide such a valved conduit in which the conduit is formed with sinuses downstream of the tri-foliate prosthetic valve, such as a natural tissue porcine xenograft valve, and which sinuses do not replicate either the natural porcine sinuses of the aortic root from which the valve is removed, for example, or the natural human aortic sinuses. However, these sinuses are especially shaped and sized to cooperate with the prosthetic valve to ensure the formation of vigorous blood-flow vortices behind each valve leaf. These vortices in the flowing blood contribute to an improved valve action, and to prompt closing of the valve leaflets upon the systole ending, as is recognized in the art. However, the vigorous vortices provided by the present inventive sinus configuration of the valved conduit also ensures that the blood-exposed surfaces of the conduit are scrubbed by the flowing blood. Consequently, blood stagnation or stasis is avoided, and clots do not form on the conduit walls to be later sloughed off as emboli in the circulatory system.

Yet another object for the present invention is to provide such a valved conduit in which the prosthetic valve, such as a porcine xenograft valve, is externally stented with the fabric of the conduit interposing between the material of the prosthetic valve and the stent structure. Consequently, the prosthetic valve is supported effectively for its operation to control the blood flow in the valved conduit to a unidirectional flow. The prosthetic valve is supported with superior strength to successfully resist the large pressure variations and rapid changes in fluid flow involved with the ventricular assist device. Further, the flowing blood is not exposed to the surfaces of the stenting structure, the formation of clots in the blood on additional blood-exposed surfaces is thus avoided and is reduced, that is, the stent structure is entirely removed from and is isolated from the flowing blood.

Accordingly, the present invention provides a ventricular assist device including a unitary flexible wall member having a singular blood-contacting inner surface entirely defining a variable-volume chamber for receiving and discharging blood, the unitary flexible wall member also defining one of an inlet port and an outflow port for respective flow of blood, and a flexible conduit member having a side wall defining a second blood-contacting inner surface and communicating blood between the variable-volume chamber and the circulatory system of a host organism, the side wall of the flexible conduit member sealingly engaging the unitary flexible wall member at the respective one of said inlet and outflow ports so that flowing blood in passing through said flexible conduit and said variable-volume chamber contacts only the first and the second blood-contacting inner surfaces.

According to a further aspect of the present invention, a valved conduit is formed of fabric sheet material having an outer surface thereof coated with impermeable polymeric material partially impregnating into the intersticial spaces of the fabric between fibers thereof toward but short of the inner surface of the fabric conduit.

Still another aspect of the present invention provides a valved conduit for a ventricular assist device including a prosthetic valve, such as a natural tissue porcine xenograft valve, defining a first blood-contacting surface, a fabric conduit in which the prosthetic valve is secured and defining a second blood-contacting surface, and sutures securing the prosthetic valve into the fabric conduit and defining a third blood-contacting surface, the valved conduit having only the first, the second, and the third blood-contacting surfaces which contact blood flowing through said conduit.

The present invention provides according to another aspect a valved conduit including cl porcine xenograft valve and defining sinuses downstream of the valve which sinuses do not replicate either the porcine sinuses or human sinuses, and which by their configuration ensure that blood flow past the leaflets of the valve forms vigorous vortices behind these leaflets without blood stagnation.

Still further, the present invention provides a valved conduit in which a resilient connection is provided between the valved conduit and adjacent blood-carrying structures. This resilient connection provides for all of post-implantation absorption of a collagen or other biodegradable transitional coating from the inner surfaces of the valved conduit with attendant dimensional changes, for the subsequent formation of a stable biological interface on these surfaces also possibly with attendant change of dimensions, and for components of the valved conduit and adjacent structure taking a set with the passage of time after surgical implantation, all without loss of sealing integrity between the connected structures. Such a loss of sealing integrity could create a leakage path at the interface of the valved conduit and an adjacent structure.

Additionally, the present invention provides such a valved conduit which is interfaced with adjacent blood-carrying structure by a polarized connection both preventing incorrect assembly of the valved conduit to the adjacent structure, and preventing damage to the conduit or adjacent structure from the application of excessive tightening force, while also accommodating changing dimensions as components of the valved conduit and adjacent structure take a set with the passage of time after surgical implantation.

Additional objects and advantages of the present invention will be apparent from a reading of the following detailed description of a single preferred embodiment of the present invention, taken in conjunction with the appended drawing Figures, in which the same reference numeral refers to the same feature in each of the various views, or to features which are analogous in structure or function.

BRIEF DESCRIPTION OF THE DRAWING FIGURES

FIG. 1 is a fragmentary frontal elevational view diagrammatically depicting a ventricular assist device according to the present invention implanted in a human host patient;

FIG. 2 provides a fragmentary cross sectional view of a portion of the ventricular assist device seen in FIG. 1, with a portion of the external housing of the device removed for clarity of illustration;

FIG. 3 provides a fragmentary exploded perspective view of the ventricular assist device with valved conduits thereof separated from a pump portion of the device in order to more clearly show a polarized connection structure for each of the valved conduits;

FIGS. 4 and 5 show respective longitudinal cross sectional views taken through the inflow and outflow valved conduits of the ventricular assist device of the present invention;

FIG. 6 provides a greatly enlarged fragmentary cross sectional view taken through the inflow conduit connection with the pump portion of the present assist device;

FIG. 7 provides an enlarged transverse sectional view taken at line 7—7 of FIG. 4;

FIG. 8 provides an enlarged fragmentary longitudinal cross sectional view taken along line 8—8 of FIG. 7;

DESCRIPTION OF AN EXEMPLARY EMBODIMENT OF THE INVENTION

Figure 1:
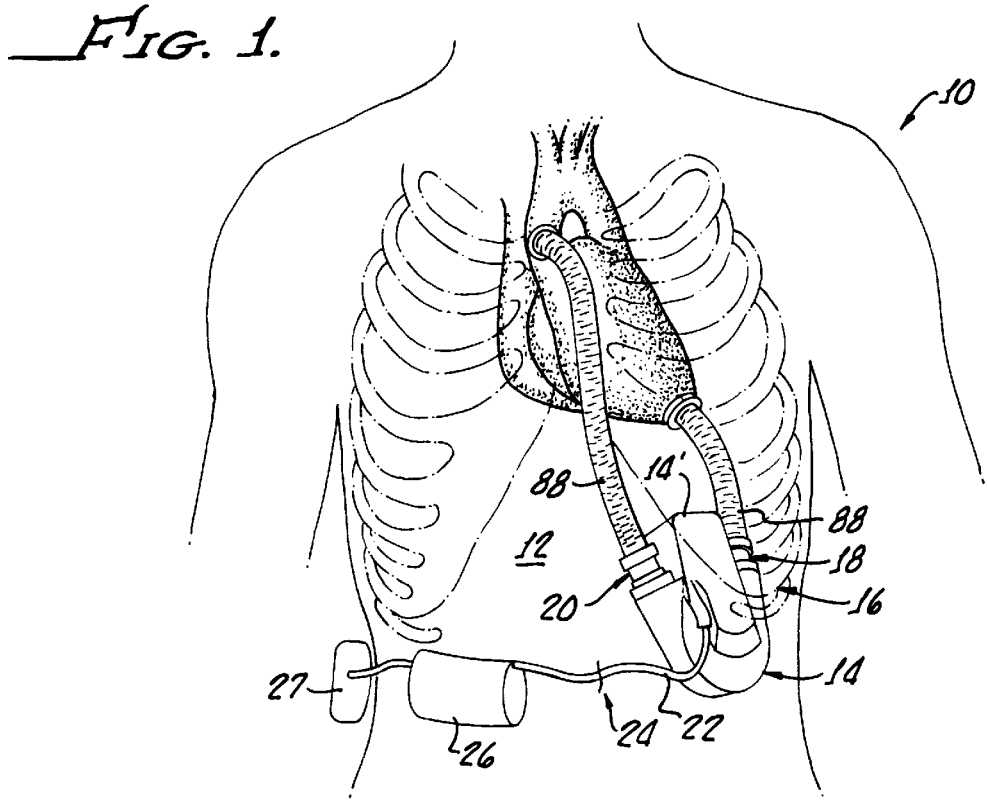

With reference first to FIG. 1 a living human host patient 10 is shown in fragmentary front elevational view, and with parts of the patient's anatomy shown in phantom or removed solely for better illustration of the salient features of the present invention. It will be understood that the human host patient 10 preferably has a complete anatomy, and that the use of the present invention does not generally require that any part of the patient's normal anatomy be removed, as might be suggested by FIG. 1.

Surgically implanted into the patient's abdominal cavity 12 is the pumping portion 14 of a ventricular assist device, generally referenced with the numeral 16. The ventricular assist device 16 includes an inflow conduit 18 communicating blood from the patient's left ventricle into the pumping portion 14, and an outflow conduit 20 communicating blood from the pumping portion 14 to the patients ascending thoracic aorta. At the end of the inflow conduit 18 which is connected to the patient's heart, and at the end of the outflow conduit 20 which is connected to the ascending thoracic aorta, these conduits are attached to the natural tissues by suture rings so that blood flow communication is established and maintained. From the pumping portion 14 a power cable 22 extends outwardly of the patient's body via an incision 24 to a compact controller 26. A power source, such as a battery pack worn on a belt about the patient's waist, and generally referenced with the numeral 27, is connected with the controller 26.

Figure 2:
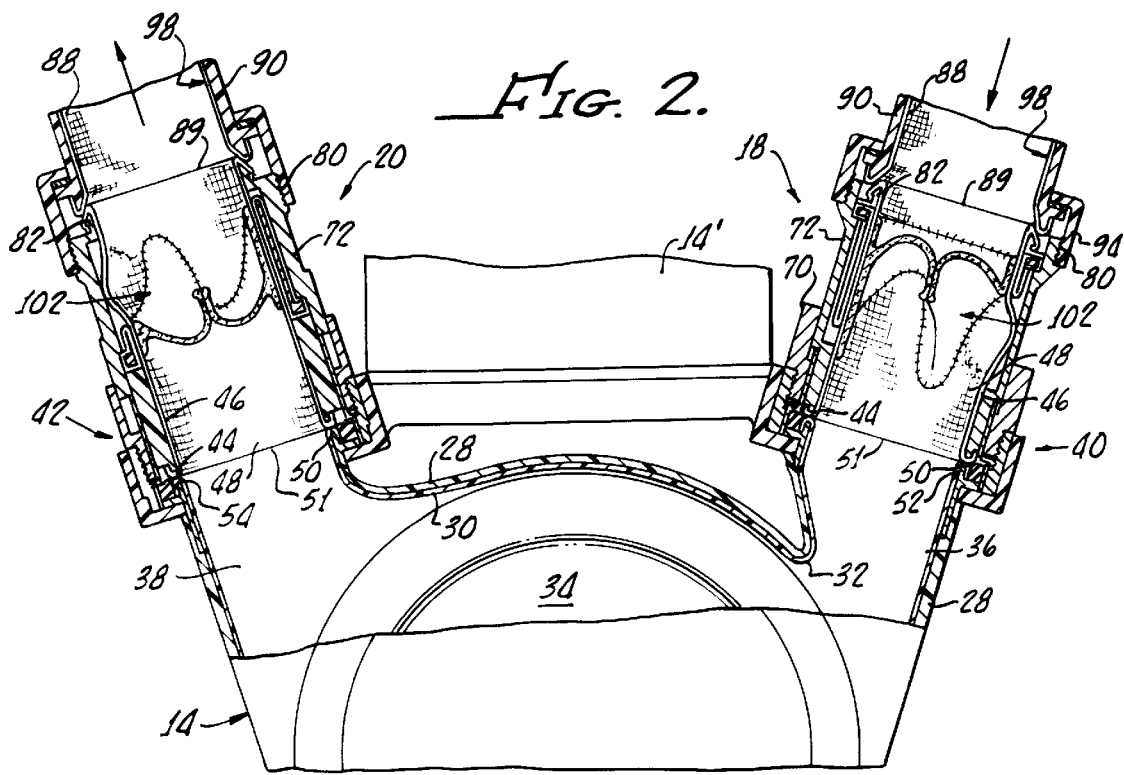

Viewing FIG. 2, it is seen that the pumping portion 14 includes a housing 28 within which is received a flexible unitary liner or bag member 30. This bag member 30 defines a singular blood-contacting inner surface 32, bounding a variable-volume chamber 34. The bag member 30 includes a diaphragm portion (not shown) which is reciprocally movable in response to reciprocating movements of a power member (referenced generally with the numeral 14') of the pumping portion 14 to expand and contract the variable-volume chamber 34. As FIG. 2 illustrates, the bag member 30 also defines tubular leg portions 36, 38, extending to and through respective inlet and outlet fitting features 40, 42 of the housing 28. At each of the inlet and outlet fitting features 40, 42, of the housing 28, the tubular legs 36, 38 form reentrant portions 44, each of which is generally J-shaped in cross section. At the inlet and outlet fitting features 40, and 42, the housing 28 includes structural provisions allowing connection and disconnection of the respective inflow and outflow conduits 18, 20, as will be further described.

Importantly, as FIG. 2 shows, each of the inflow and outflow conduits 18, 20, respectively includes a tubular flexible, but shape-retaining fabric-composite inner wall member 46, having an inner blood-contacting surface 48. As will be further explained, the inner blood-contacting surfaces 48 of the conduits 18 and 20 each also defines a respective reentrant end portion 50. The reentrant end portions 50 are also J-shaped in cross section. As is seen in FIG. 2, the reentrant end portions 50 of the conduits 18 and 20 sealingly contact the reentrant portions 44 of the bag member 30. These sealingly contacting reentrant portions 44 and 50 cooperatively define a sealing line 51. Consequently, the flowing blood in moving from the inflow conduit 18 to the bag 30, and from this bag to the outflow conduit 20, crosses only two material-surface transitions. The first of these material-surface transitions is from the surface 48 of the inner wall member 46 at the inflow conduit 18 to the surface 32 of the bag 30, the second of these material-surface transitions is from the surface 32 to the surface 48 of the conduit 46 at the outflow conduit 20. As will be further described and explained, this minimizing of material-surface transitions which are exposed to flowing blood in the ventricular assist device 16 is a consistent feature throughout the device.

Figure 3:
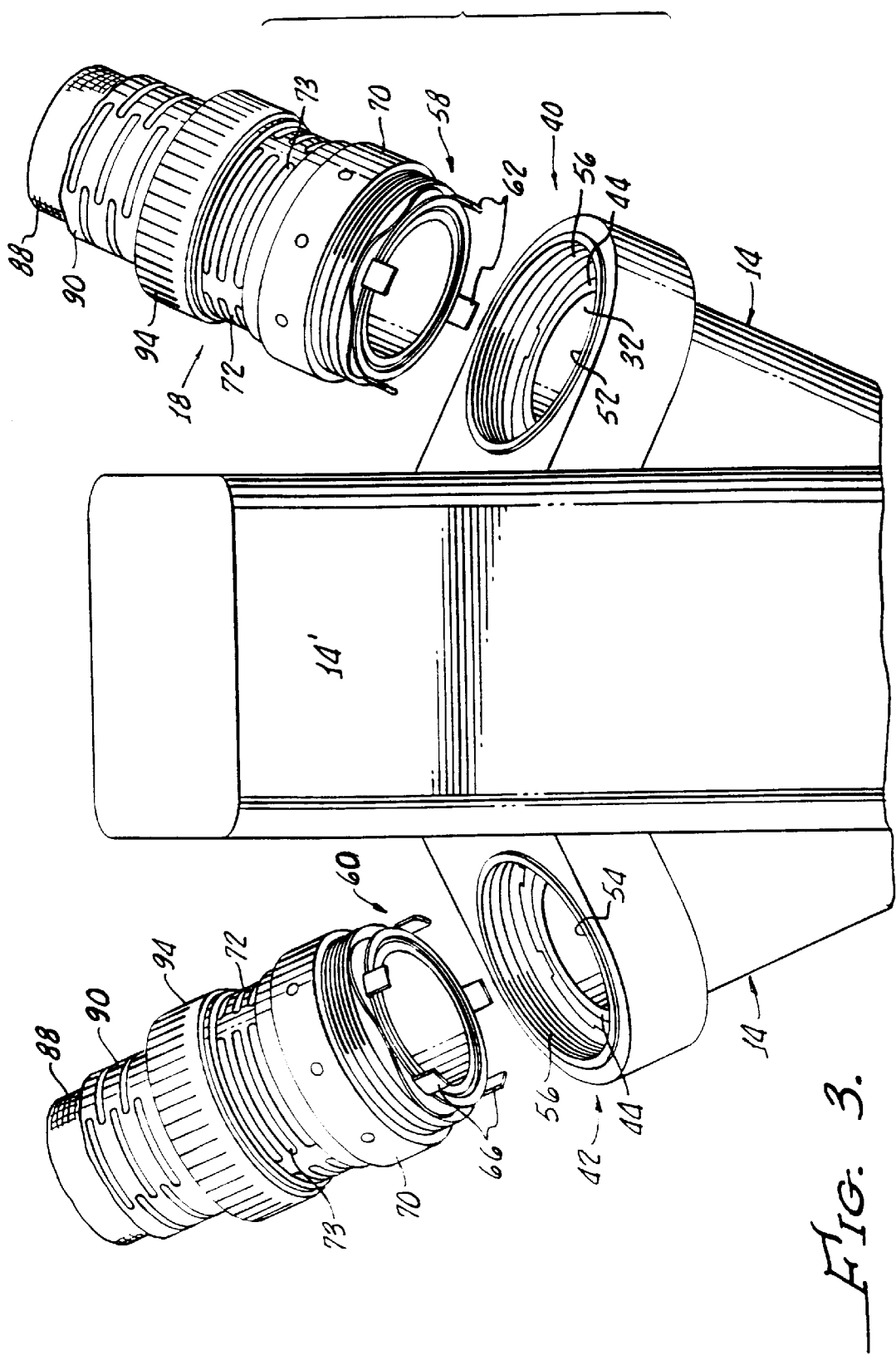

FIG. 3 provides a fragmentary exploded perspective view of the pumping portion 14, and of the two blood flow conduits 18, and 20, as they may appear, for example, during surgical implantation of the assist device 16. FIG. 3 illustrates that as part of the fitting features 40 and 42, the housing 28 defines a respective inflow port 52 and a respective outflow port 54, each with a respective female threaded recess 56 leading to the corresponding one of the exposed reentrant portions 44 of the bag 30. These threaded recesses 56 are in most respects identical with one another. That is, they define the same diameter, and have the same type and pitch of screw thread. However, the fluid flow configuration of the pumping chamber 34, and of the transitions of the legs 36 and 38 into and from this chamber, is different for the inflow port than for the outflow port because of the differing pressure and momentum conditions for the flowing blood passing through these leg portions of the bag 30. Accordingly, the physician must properly connect the inflow conduit 18 to the inflow port 52, and the outflow conduit 20 to the outflow port 54.

In order to insure that the implantation physician does not mistakenly connect the conduits, each conduit includes a respective exclusive-fitting key feature 58, 60. The inflow conduit key feature 58 includes four axially extending and circumferentially evenly spaced key elements 62. At the inflow port 52, the recess 56 of housing 28 defines four matching slots 64. The outflow conduit key feature 60 includes five axially extending and circumferentially evenly spaced key elements 66. At the outflow port 54, the recess 56 of housing 28 defines five matching slots 68. Each of the conduits 18, 20 includes a knurled and male-threaded connector collar 70, which is freely rotatable on the end of the conduit to be connected to the pump housing 28. This collar 70 is threadably receivable into the recesses 56. Consequently, the physician can connect the valved conduits 18, 20 to the housing 28 of the pumping portion 14 of the assist device by feel alone if necessary.

That is, in the environment of the surgical implantation, the physicians need not rely on color coding or some other visual device to assures themselves that the conduit connections are being effected correctly. The conduits 18, 20 will mate with the housing 28 only in the proper location, and this proper mating of the conduits with the housing can be determined by the tactile feel of the keys 62 and 66 dropping into the slots 64 and 68 when the connections are made properly. When these proper connections are made, then the threaded collars 70 will threadably engage the threads of the corresponding recess 56 to retain the conduit connections.

Figure 4:
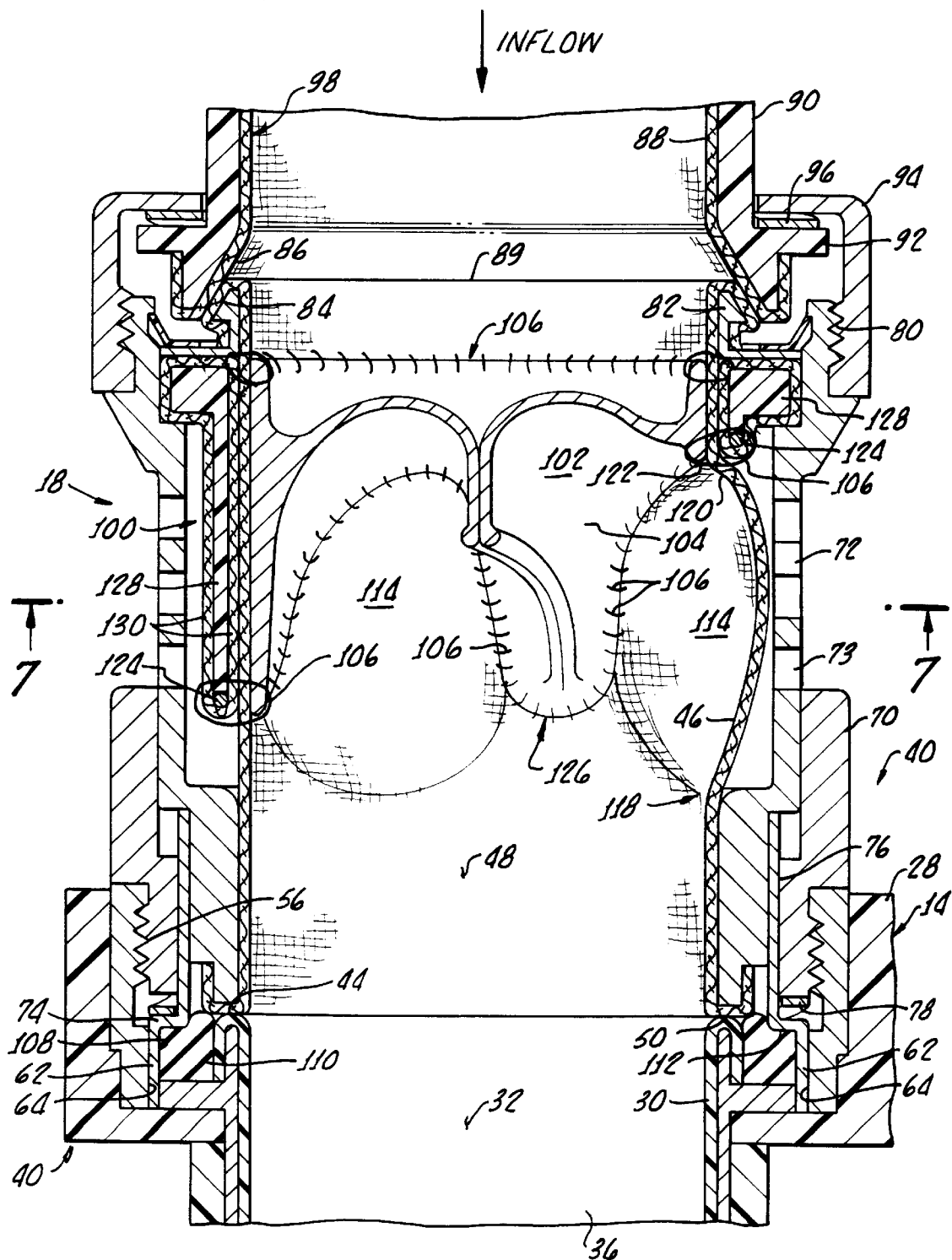
Figure 5:
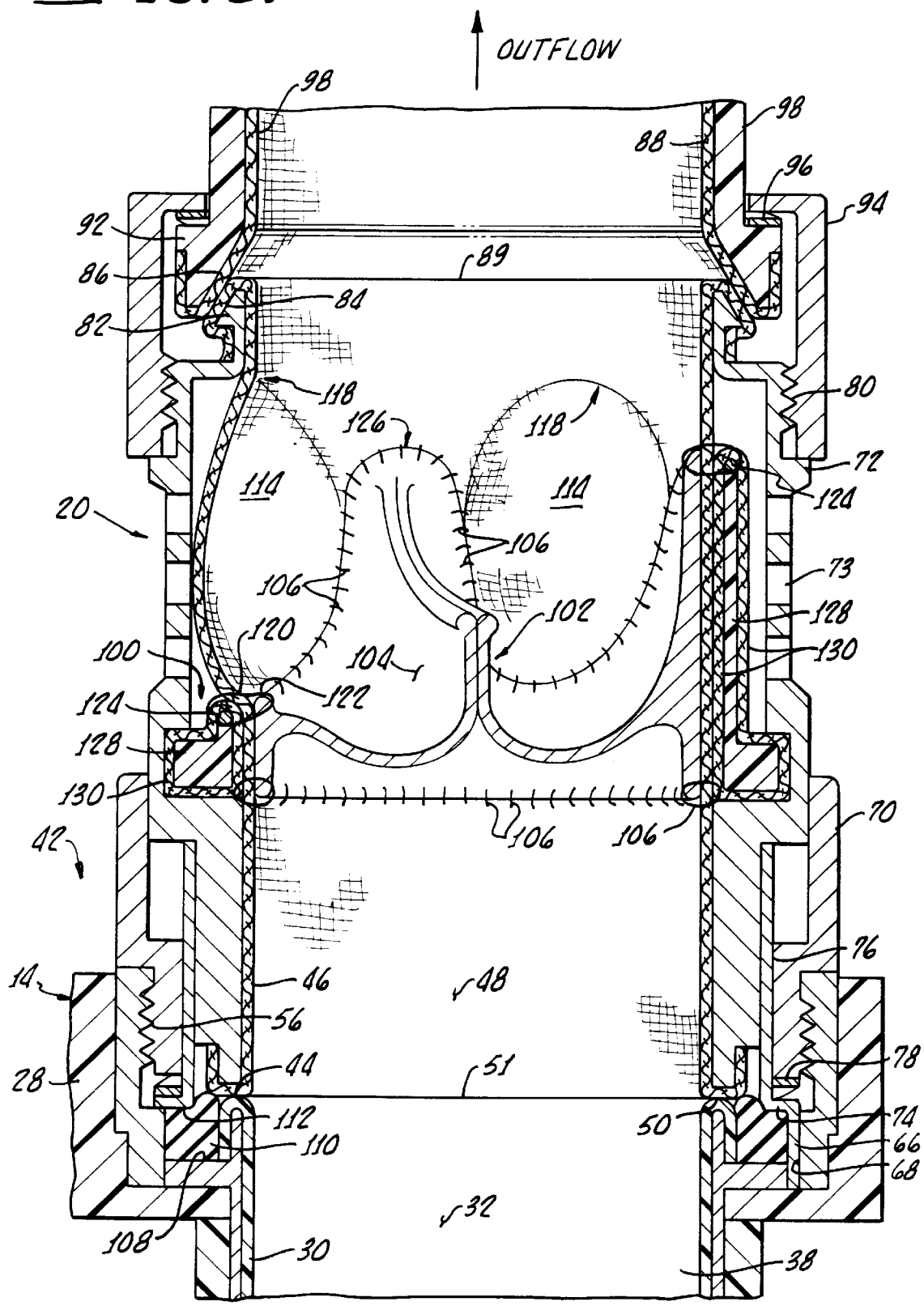

FIGS. 4 and 5 provide respective axial cross sectional views through the respective inflow and outflow conduits 18 and 20. Because many of the features of these two conduits are the same, they are described together, and the same reference numeral is used with respect to features of each which are the same or which are analogous in structure or function to one another. Each of the conduits 18, 20 includes a tubular metallic housing 72. This housing is flanged at 74, and defines an outward cylindrical portion 76 upon which the collar 70 is rotationally carried, viewing also FIG. 6. Interposed between the collar 70 and the flange 74 is a circumferentially extending wave washer 78, the purpose of which will be described below. However, viewing FIGS. 4 and 5, and recalling the description above, it is apparent that when the collars 70 are threaded into the recesses 56 of the housing 28 they confront the flanges 74 to retain the conduits 18, 20, with the reentrant end portions 50 in sealing engagement with the reentrant portions 44 of bag 30 to define the singular sealing lines 51. The housings 72 define plural perforations 73, in the form of slots, to allow body fluid tc, access the internal surfaces of these housings and avoid the formation of cavities or voids which are hidden from the immune system.

At the end of each housing 72 of conduits 18, 20 distally from the pumping portion 14, a male-threaded portion 80 circumscribes a tapered seating feature 82. On the tapered seating feature 82 with an interposed radially extending annular portion 84 of the inner wall 46 is sealingly connected the adjacent end 86 of an elongate flexible polyethylene terephthalate fabric blood conduit 88. The conduits 88 lead to the pumping portion 14 from the patient's left ventricle, and from this pumping portion to the patient's ascending aorta. The ends of these conduits 88 remote from the pumping portion 14 are sutured to the heart and aorta at appropriate incisions in each to achieve communication of the conduits 18, 20, and of the pumping portion 14 with the patient's circulatory system. The end 86 of the conduit 88, and the portion 84 of inner wall 46 sealingly engage one another to cooperatively define the sealing line 89.

Around the polyethylene terephthalate fabric blood conduit 88 is a flexible plastic sheath 90. This plastic sheath 90 defines an end shoulder 92, and rotationally carries an internally-threaded collar 94. Collar 94 threadably engages the thread portion 80 of the housing 72 to maintain sealing engagement of the conduit 88 with the portion 84 of the inner wall 46 at the tapered seating feature 82. Interposed between the collar 94 and the end shoulder 92 is a circumferentially extending wave washer 96. On the inner surface of each polyethylene terephthalate fabric blood conduit is a thin bio-compatible collagen coating, indicated with arrowed lead line 98. This collagen coating serves to make the polyethylene terephthalate fabric conduit 88 more leak resistant at the time of implantation, and also more compatible with the patient's blood.

However, this collagen coating 98 is biodegradable, and is eventually absorbed by the patient's body. At the same time that the collagen coating 98 is being absorbed by the patient's body, a biological interface is deposited on the inner surfaces of the conduits 88. As the collagen coating 98 is absorbed from the area of conduit 88 at the end 86 seating on wall portion 84 and seating feature 82, the dimensions of the conduit 88 may decrease slightly. This slight change of dimension could lead to a blood seepage at the connection of the polyethylene terephthalate fabric conduits 88 to the metallic housings 72 perhaps weeks or months after the surgical implantation of the assist device 16. To avoid this possibility, the wave washer is provided so that the connection between the conduits 88 and the housings 72 has; an axial resilience accommodating changes in thickness dimensions of the conduits. Also, this axial resilience provides for maintenance of sealing engagement between the conduits 88 and the housings 72 as these parts take a set over time following implantation.

With attention now more particularly to the fabric-composite tubular inner wall member 46, it will be noted that this inner wall member defines the inner surface 48, which extends continuously between and is integral with the reentrant end portion 50 at the housing 28 (which is sealingly engaged by bag member 30 at sealing line 51) and the radially extending portion 84 (which is sealingly engaged by the fabric conduit 88 at sealing line 89). This inner surface 48 defines the blood-contacting boundary for the conduits 18, 20. Within this inner surface 48, and secured to the fabric of the fabric-composite inner wall member 46, and to an external stent structure 100, is a porcine xenograft tri-foliate valve 102. It will be understood that other types of prosthetic valve may be used in the conduits 18 and 20. For example, one type of prosthetic valve now available is fashioned from a sheet of either animal or human tissue, or from artificial material. This and other types of prosthetic valves may be used in the present invention. This xenograft valve defines tissue surfaces 104. In the inflow conduit 18, the valve 102, and supporting stent structure 100, are disposed for unidirectional blood flow toward the chamber 34. In the outflow conduit, the valve 102 and supporting stent structure 100 are oppositely disposed. The porcine xenograft valve 102 is secured to the inner wall 46 and to stent structure 100 by sutures 106. Accordingly, it is seen that blood flow through the conduits 18, 20, contacts only the inner surface 48 of conduit 46, the tissue surface 104 of the xenograft valve 102, and the sutures 106.

Figure 6:
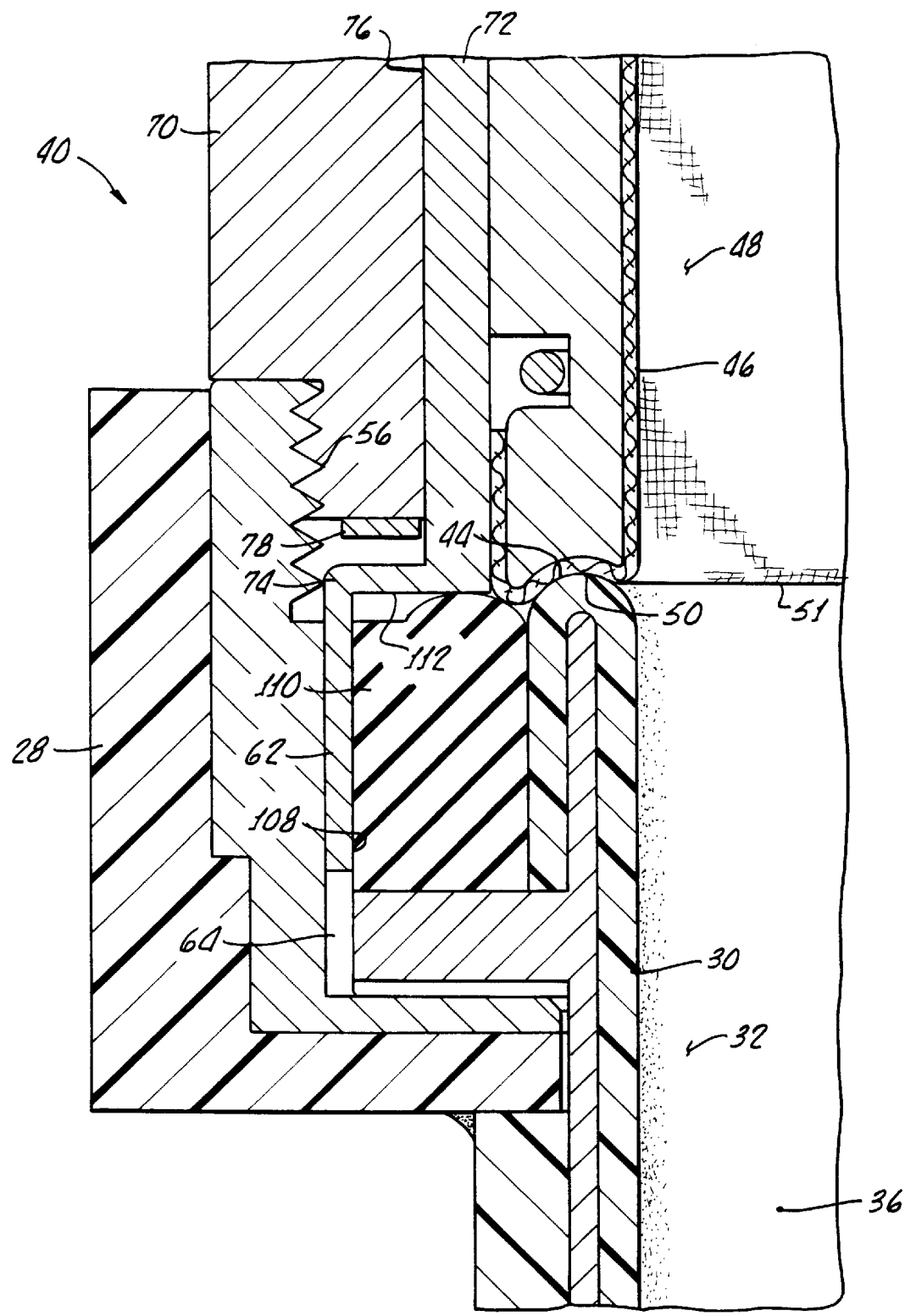

Returning to a consideration of FIG. 6, it is seen that within the recess 56, the housing 28 also defines an additional annular recess 108. Disposed in this recess 108 is an annular elastomeric sealing member 110. When the conduit 18 or 20 is received into the respective one of the recesses 56, the reentrant portion 50 of the inner wall member 46 sealingly engages with the reentrant portion 44 of the pumping bag member 30. This sealing interface is inwardly exposed to flowing blood. However, radially outwardly of the sealing interface of surfaces 44 and 50, the sealing member 110 is sealingly engaged by an end edge surface 112 of the housing 72 in order to provide a redundant secondary sealing interface between the conduits 18, 20 and the housing 28. This secondary sealing feature (member 110 and metallic end edge surface 112) is not exposed to flowing blood. Also, as is seen in FIG. 6, the housing 28 at recess 56 defines a slot 64 for receiving a respective one of the exclusive-fitting keys 62. This same feature is found at the recess 56 for the conduit 20, recalling that the number of keys, and slots for these keys, differs between the recess 56 for inflow conduit 18 and the recess 56 for outflow conduit 20.

Figure 7:
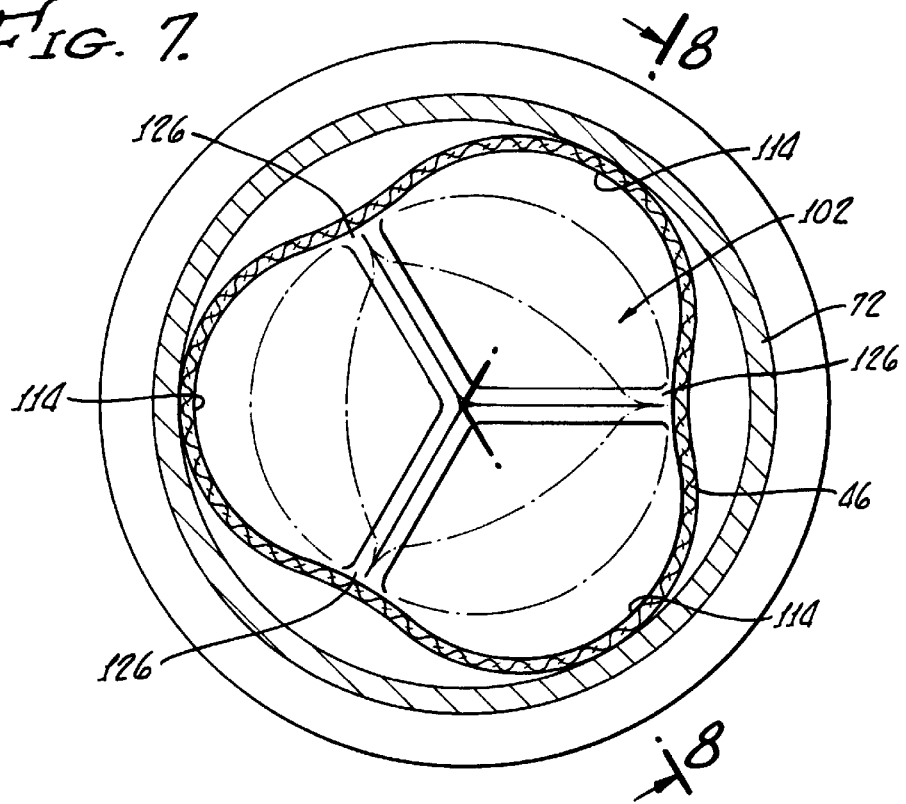
Figure 8:
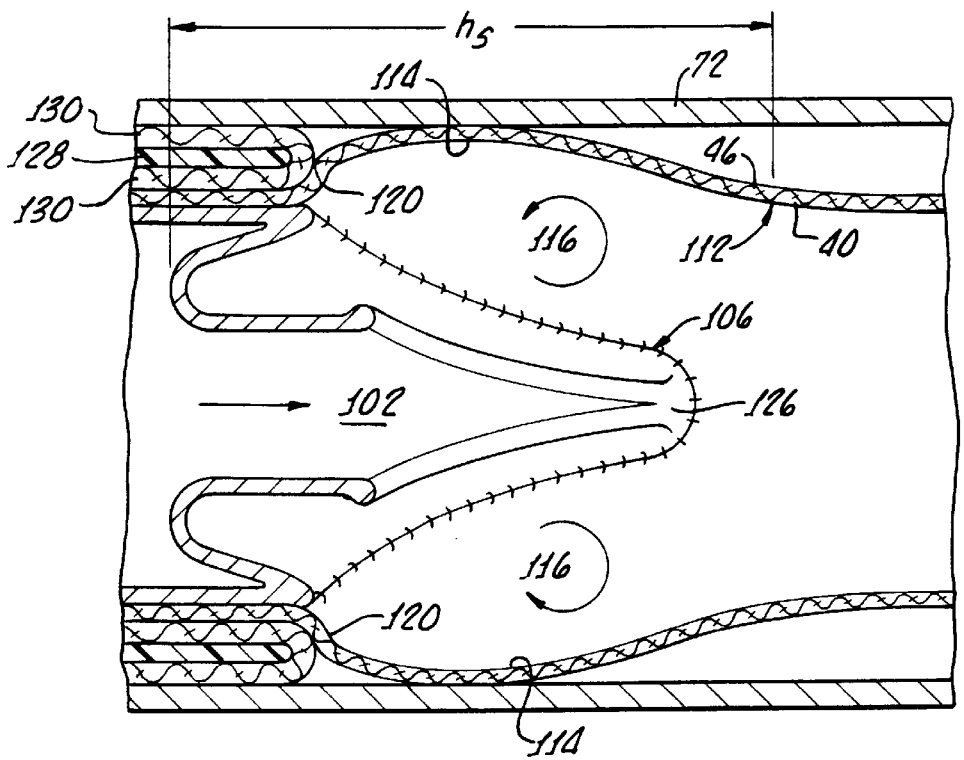

Returning to consideration of FIGS. 4 and 5, immediately downstream of the xenograft valve 102, the tubular inner wall member 46 defines three out-bulgings, or sinuses 114. These sinuses 114 are aligned axially with each one of the three valve leaflets of the valve 102, viewing also FIGS. 7 and 8. As is understood in the art, a sinus at this location having a downstream termination which is located somewhat downstream of the leaflets in their open positions (viewing FIG. 8), promotes the entry into the sinuses of a flow vortex 116 formed at the downstream end of the valve leaflets. This vortex flow contributes to a prompt closing of the valve at the end of the systole with little regurgitation.

However, the natural porcine or human sinuses are considerably larger than the Applicants; have determined to be optimum for use with the prosthetic valve 102. In fact, the natural human sinuses at the aortic valve form a circular boundary with the valve leaflet if viewed in an oblique plane extending perpendicularly to the axis of the leaflet surface. Also, in a transverse plane the natural human sinuses are pouch-like and at their maximum dimension define a diameter almost twice the diameter of the aorta. The sinuses 114 of the conduits 18 and 20 are smaller than natural sinuses, and rejoin the generally cylindrical tubular inner wall member 46 at an acute or glancing angle, indicated with the arrowed lead line 118. Further, the sinuses 114 are longer and shallower than natural sinuses, as is explained below.

More particularly, if the inner valve leaflet radius at the base of the tri-foliate valve 102 is referred to as $R_b$, and the radius at maximum dimension of the sinuses 114 is referred to as $d_s$, with the length of the sinuses 114 from the attachment of the valve leaflets to the rejoining of the sinus wall with the projected cylindrical shape of the remainder of the inner wall 46 (i.e., at the arrow 112) being referred to as $h_s$ (viewing FIGS. 7 and 8), then for natural sinuses of several mammalian species, including rabbits, canine, ox, sheep, calf, pig, and human an aspect ratio of $h_s$ divided by $d_s$ can be calculated. The dimensions of usual aortic valves for these species is found in the literature. It is seen that the ratio value naturally ranges from 0.71 to 1.2. For the conduits 18 and 20, the aspect ratio of the sinuses 114 is in the range from at least about 1.3 to about 1.6 or more. More preferably, the aspect ratio for the sinuses 114 is about 1.45.

The Applicants have determined that the above-described range of sinus aspect ratios is preferable for achieving vigorous vortex blood flow downstream of the valve 102 in the inflow conduit 18, with resulting elimination of blood stasis or stagnation. Blood flow into the pumping portion 14 via this conduit 18 results merely from the natural blood pressure prevailing in the circulatory system of the host patient 10. The variable-volume pumping chamber 34 does not effectively aspirate blood into this chamber by expansion. Instead, blood flows by its own pressure through the conduit 18 and into this chamber, expanding the chamber 34. Accordingly, the inflow of blood via conduit 18 is comparatively slow. The increased aspect ratio of the conduit 18 in comparison with the natural sinuses is important to the prevention of clot formations in the conduit 18.

On the other hand, the blood flow out of pumping chamber 34 is forceful and vigorous. A sinus configuration at conduit 20 which replicated the natural sinuses might be acceptable. However, as pointed out above, the natural sinuses are more bulged out and take up more room. The sinus shape of the present invention with an aspect ratio of at least 1.3 or higher, when used also at the outflow conduit 20, results in an outflow conduit of smaller diameter, reduces the size of the apparatus implanted into the host patient 10, and serves very well to promote vigorous blood vortex flow downstream of the valve 102 without the formation of clots in the conduit 20.

As will be further explained, the tubular fabric-composite inner wall member 46 is formed with the sinuses 114, and with adjacent arcuate transition portions 120, transitioning between a downstream edge 122 of the xenograft valve 102 and the sinuses 114, viewing FIGS. 4 and 5. These transition portions 120 allow the xenograft valve 102 to be externally stented with the stent structure 100 being located outside of the flexible fabric tubular inner wall member 46, while still providing a smooth surface for blood flow transition from the xenograft valve 102, to the surface 48 of the wall member 46 downstream of the valve 102. The stent structure 100 includes a metallic wire-form 124 having three axially-extending commissure support parts, which are not visible in the drawing Figures, but which align with and follow the shape of the natural commissures 126 of the porcine xenograft valve 102. Received in the wire-form 124 is a polyester support member 128. Around the wire-form 124, and the support member 128, is formed a fitted polyethylene terephthalate fabric drape 130. The polyethylene terephthalate fabric drape 130 is formed closely to the wire-form 124 and support member 128. However, sutures 106 engage this drape 130 and the underlying wire-form 124, pass through the corresponding inner wall member 46, and secure the tissue xenograft valves 102 in the conduits 18, 20, respectively. The fabric composite inner wall member 46 is also formed with very slight recesses between the sinuses 114, which recesses accommodate the radial thickness of the commissures of the wire-form 124.

Figure 9:
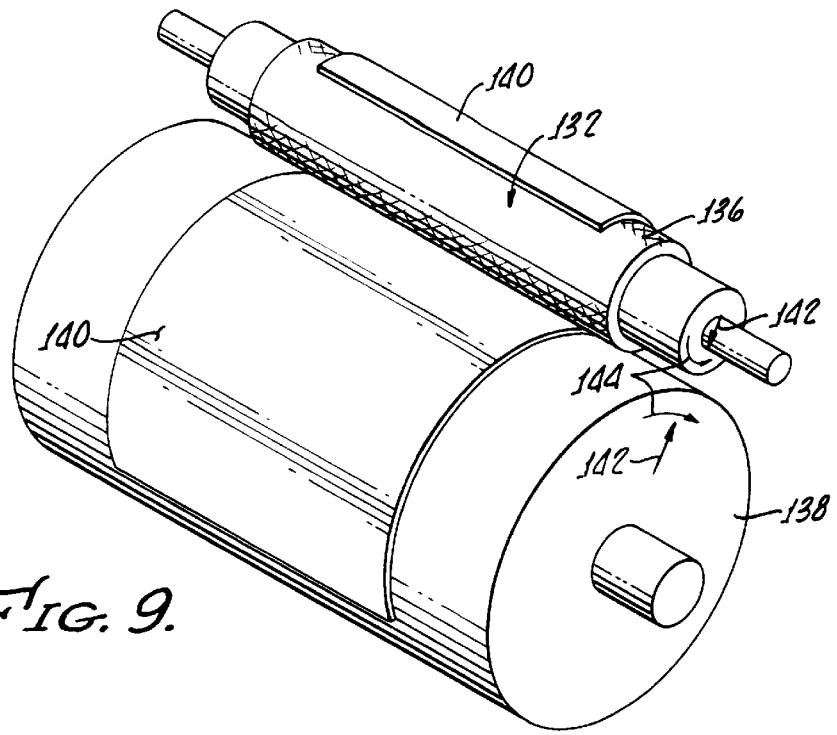
FIG. 9 is a somewhat diagrammatic presentation of a step in the process of manufacturing a valved conduit according to the present invention.
Figure 10:
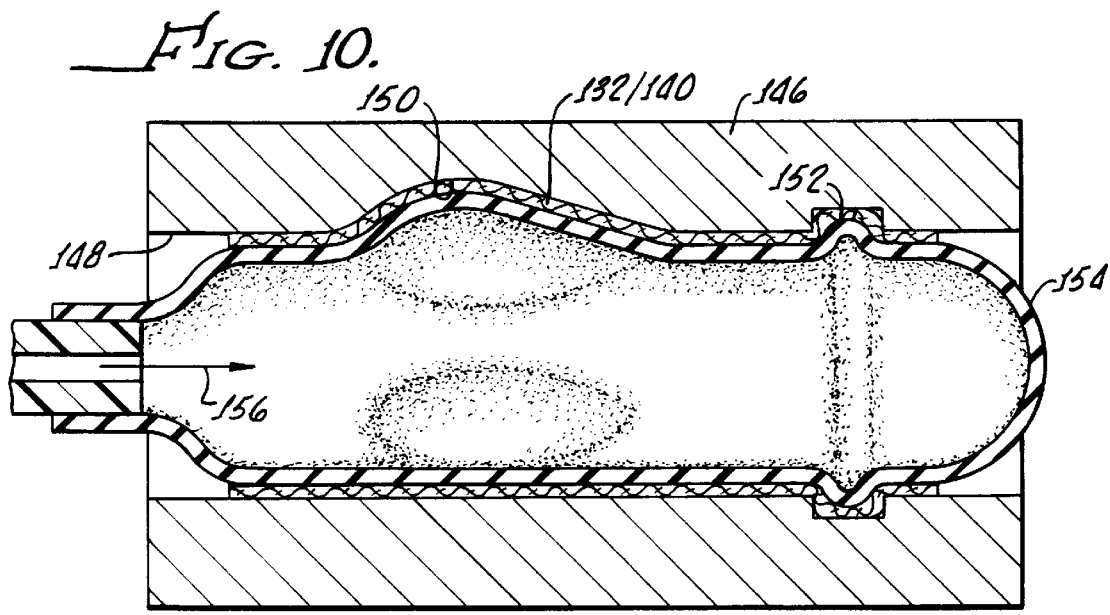
FIG. 10 is a somewhat diagrammatic and cross sectional view of a step of the manufacturing process for making a valved conduit according to the present invention, and is subsequent to the step seen in FIG. 9.
Figure 11:
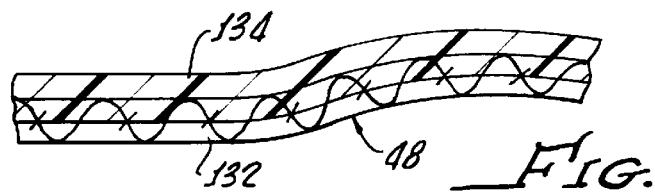
FIG. 11 is a greatly enlarged and somewhat schematic representation of an inwardly porous, but blood-impermeable, fabric resulting from the manufacturing steps seen in FIGS. 9 and 10, and which forms a wall of the valved conduit of the present invention.

Considering now FIGS. 9, 10, and 11, the first two of these Figures show steps in the process of making a flexibly shape-retaining fabric-composite tubular inner wall member 46 for a valved conduit, such as conduit 18 or 20. FIG. 11 shows a greatly enlarged cross sectional view through the fabric-composite tubular inner wall member 46. As FIG. 11 shows, this inner wall member 46 includes a single ply of tubular-woven and/or knitted polyethylene terephthalate fabric 132. Even though this woven and/or knitted fabric 132 is of made of fine-dimension fibers, and is closely woven or knitted, it nevertheless is liquid permeable. Consequently, the fabric 132 is porous, and must be considered to be substantially blood permeable. However, in order to render the inner fabric composite wall 46 substantially blood impermeable while still providing a porous inner surface 48 to which a stable biological interface may attach, the tubular fabric 132 is transfer-coated externally with sheet silicone rubber material 134.

As FIG. 11 shows, this silicone rubber 134 is permeated inwardly into and partially through the woven or knitted fabric 132, toward but short of the inner surface 48 of this fabric. The silicone rubber 134 is axially and circumferentially continuous, so that it forms a liquid-impermeable barrier or membrane integral with the fabric 132, and an integral part of the inner wall member 46. Inwardly of this silicone rubber 134, the woven and/or knitted fabric 132 through a part of its thickness still forms a filamentary permeable structure providing a porous inner surface (i.e., the inner surface 48 of the conduit 46), into which a stable biological interface may implant. This surface 48 is still porous like conventional woven and/or knitted polyethylene terephthalate fabric vascular grafts, but the porosity of the fabric no longer extends completely through the thickness of the fabric 132.

Viewing FIG. 9 it is seen that the tubular woven and/or knitted fabric 132 in a limp cylindrical configuration without the silicone rubber 134, sinuses 114 or other features, is placed on a cylindrical mandrel 136. Adjacent to this mandrel 136 is disposed a cylindrical roller 138 with a smooth hard surface. On the roller 138 is disposed a sheet 140 of raw silicone rubber material. The mandrel 136 and roller 138 are pressed together (indicated by arrows 142) while being rotated in unison (indicated by arrows 144) to transfer the silicone rubber sheet material 140 onto and into the woven and/or knitted fabric 132. By control of the state of the silicone rubber material of sheet 140 (i.e., its degree of partial curing), and the amount of pressure applied, the degree or depth of penetration of the silicone rubber material into the woven or knitted fabric 132 is controlled. The woven or knitted fabric material 132 and silicone sheet material 140 are then removed together from the mandrel 136. Subsequently, the silicone material 140, which is a thermoset material, is completely, or substantially completely cured to produce as a manufacturing intermediate article or work piece, a cylindrical sleeve of woven or knitted fabric outwardly coated and partially impregnated with silicone rubber.

Next, the work piece including the cylindrical woven or knitted fabric sleeve 132 and silicone rubber 140, referred to in FIG. 10 with the composite reference numeral 132/140, is placed into a heated female-cavity mold 146. This mold 146 defines a cavity 148 generally matching to the cylindrical shape of the work piece 132/140, but also having radially outwardly extending recesses 150 corresponding to the sinuses 114, slight indentations between the recesses 150 for accommodation of the commissures of the wire-form 124, and one or more circumferential grooves or diametral steps 152, which will form the reentrant surface 50 or annular portion 84 of the fabric-composite inner wall member 46, recalling FIGS. 4 and 5. Into the cavity 148 and within the tubular work piece 132/140 is placed a thin-walled high-pressure expansible balloon 154. This balloon is made of an elastomeric material, such as a vulcanized natural or synthetic rubber, which is able to withstand both an elevated temperature and internal pressure. The balloon 154 is inflated by applying an internal pressure (indicated with arrow 156) to force the work piece 132/140 against the inner surfaces of the cavity 148.

Even though the silicone rubber 140 of the work piece 132/140 is a thermoset material, and is at least substantially cured, the polyethylene terephthalate fabric 132 is a thermoplastic material. Consequently, the work piece 132 takes on and retains a shape replicating the internal shape of the cavity 148. The cavity 148 is cooled, the balloon 154 is deflated to return it to its original size for removal from the cavity 148, and the work piece is removed from this cavity. Although the polyethylene terephthalate fabric material 132 is a thermoplastic material and is changed in shape by the above-described process, at least in the area of the sinuses and at the features 50 and 81 of the inner fabric composite wall member 46, the penetration or impregnation of the silicone rubber 140 partially through this fabric is substantially not changed. The silicone rubber was cured fully or substantially enough before this shaping step so that the silicone rubber is no longer mobile in the fabric 132 of the work piece 132/140. This work piece 132/140, having woven and/or knitted fabric 132 with silicone rubber liquid barrier 134, is substantially ready for use in making the fabric composite inner wall member 46. Subsequently, the work piece 132/140 is trimmed to fit into the conduit 18 or 20, the xenograft valve 102, and stent 100 is added, and the combination is placed into the housing 72 and completed at the ends for sealing cooperation with the pump portion 14 and conduits 88, as described above.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. A ventricular assist device for implantation in a human host, comprising:

a pump including a rigid housings and a flexible unitary liner within the housing defining a variable volume chamber;

inflow and outflow openings to the variable volume chamber defined by tubular co-extensions of the pump housing and inner unitary liner, each of the inflow and outflow openings terminating in a circular first sealing surface formed by wrapping the unitary liner back upon the housing;

inflow and outflow conduits attached, respectively, to the inflow and outflow openings of the pump, each conduit having opposed open ends and being adapted to channel blood between the variable volume chamber and a host circulatory system, each conduit having a rigid, generally tubular housing, a flexible tubular wall member within the conduit housing, and a circular second sealing surface on one end having approximately the same diameter as the first sealing surface and formed by wrapping the wall member back upon the conduit housing; and attachment structures for connecting the inflow conduit to the inflow opening and the outflow conduit to the outflow opening so that the first sealing surfaces axially abut and compress against the second sealing surfaces to define therebetween conduit/pump inflow and outflow sealing lines, wherein blood flowing from the inflow conduit across the conduit/pump inflow sealing line into the variable volume chamber and then across the conduit/pump outflow sealing line to the outflow conduit only contacts the flexible tubular wall members of the conduits and the unitary liner of the pump.

2. The device of claim 1, further including a biasing member provided as part of each of the attachment structures connecting the inflow conduit to the inflow opening and the outflow conduit to the outflow opening, the biasing member positioned to apply an elastic force urging each pair of first and second sealing surfaces toward one another and maintain a consistent blood-tight seal at the conduit/pump inflow and outflow sealing lines.

3. The device of claim 2, wherein the attachment structures each include a pump coupling member connected to the pump housing aid a conduit coupling member connected to the conduit housing, wherein one of the pump coupling member or conduit coupling member has a pair of axially facing and relatively displaceable surfaces, and wherein the biasing members are axially elastic and placed in compression between the axially facing surfaces to apply the elastic force.

4. The device of claim 3, wherein the biasing members are wave washers.

5. The device of claim 3, wherein the pump coupling member and conduit coupling member include mating threads and are screwed together.

6. The device of claim 1, wherein each conduit includes a circular third sealing surface on the opposite end from the second sealing surface, the third sealing surface being formed by wrapping the wall member back upon the conduit housing and wherein the device further includes:

inflow and outflow flexible conduit extensions adapted to communicate blood between the host circulatory system and the inflow and outflow conduits, respectively, each extension comprising an inner flexible blood conduit coaxially disposed within an outer plastic sheath terminating in a rigid circular end portion, and including a circular fourth sealing surface having approximately the same diameter as the third sealing surface and formed by wrapping the flexible blood conduit back upon the end portion; and attachment structures for connecting the inflow conduit extension to the inflow conduit and the outflow conduit extension to the outflow conduit so that the third sealing surfaces abut and compress against the fourth sealing surfaces to define therebetween conduit/extension inflow and outflow sealing lines, wherein blood flowing across each of the conduit/extension inflow and outflow sealing lines only contacts the flexible tubular wall members of the conduits and the flexible blood conduits of the extensions.

7. The device of claim 6, further including a biasing member provided as part of each of the attachment structures connecting the inflow conduit extension to the inflow conduit and the outflow conduit extension to the outflow conduit, the biasing member positioned to apply an elastic force urging each pair of third and fourth sealing surfaces toward one another and maintain a consistent blood-tight seal at the conduit/extension inflow and outflow sealing lines.

8. The device of claim 7, wherein the attachment structures each include an extension coupling member connected to the circular end portion and a conduit coupling member connected to the conduit housing, wherein one of the extension coupling member or conduit coupling member has a pair of axially facing and relatively displaceable surfaces, and wherein the biasing members are axially elastic and placed in compression between the axially facing surfaces to apply the elastic force.

9. The device of claim 8, wherein the biasing members are wave washers.

10. The device of claim 8, wherein the extension coupling member and conduit coupling member include mating threads and are screwed together.

11. The device of claim 1, further including a prosthetic valve disposed within each of the inflow and outflow conduits and sutured to the wall member so that blood flowing through either of the inflow or outflow conduits contacts only the flexible tubular wall member, the prosthetic valve, and the sutures.

12. The device of claim 11, further including a flexible external stent provided for each of the inflow and outflow conduits between the respective conduit housings and flexible wall members, the stent being sutured to the flexible wall members and to the prosthetic valve within the conduit to support the valve therein.

13. The device of claim 12, wherein the prosthetic valve is a trifoliate natural tissue valve, having three commissures, and wherein the external stent includes a metallic wireform having three axially-extending commissure supports aligned with each commissure of the natural tissue valve.

14. The device of claim 1, wherein the wall member is a fabric sheet material having an outer surface coated with a blood-impermeable biologically-compatible material and an inner porous surface to provide a site for growth of a biological interface.

15. A ventricular assist device for implantation in a human host, comprising:

a pump including a rigid housing and a flexible unitary liner within the housing defining a variable volume chamber;

inflow and outflow openings to the variable volume chamber defined by tubular co-extensions of the pump housing and inner unitary liner, each of the inflow and outflow openings terminating in a circular first sealing surface formed by the unitary liner;

inflow and outflow conduits attached, respectively, to the inflow and outflow openings of the pump, each conduit having opposed open ends and being adapted to channel blood between the variable volume chamber and a host circulatory system, each conduit having a rigid, generally tubular housing, a flexible tubular wall member within the conduit housing, and a circular second sealing surface on one end formed by the wall member;

attachment structures for connecting the inflow conduit to the inflow opening and the outflow conduit to the outflow opening so that the first sealing surfaces abut and axially compress against the second sealing surfaces to define therebetween conduit/pump inflow and outflow sealing, lines, wherein blood flowing from the inflow conduit across the conduit/pump inflow sealing line into the variable volume chamber and then across the conduit/pump outflow sealing line to the outflow conduit only contacts the flexible tubular wall members of the conduits and the unitary liner of the pump; and a biasing member provided as part of each of the attachment structures connecting the inflow conduit to the inflow opening and the outflow conduit to the outflow opening, the biasing member positioned to apply an elastic force urging each pair of first and second sealing surfaces toward one another and maintain a consistent blood-tight seal at the conduit/pump inflow and outflow sealing lines, wherein the attachment structures each include a pump coupling member connected to the pump housing and a conduit coupling member connected to the conduit housing, wherein one of the pump coupling member or conduit coupling member has a pair of axially facing and relatively displaceable surfaces, and wherein the biasing members are axially elastic and placed in compression between the axially facing surfaces to apply the elastic force.

16. The device of claim 15, wherein the biasing members are wave washers.

17. The device of claim 15, wherein the pump coupling member and conduit coupling member include mating threads and are screwed together.

18. The device of claim 15, wherein each conduit includes a circular third sealing surface on the opposite end from the second sealing surface, the third sealing surface formed by the wall member, and wherein the device further includes:

inflow and outflow flexible conduit extensions adapted to communicate blood between the host circulatory system and the inflow and outflow conduits, respectively, each extension comprising an inner flexible blood conduit coaxially disposed within an outer plastic sheath terminating in a rigid circular end portion, and including a circular fourth sealing surface formed by the flexible blood conduit; and attachment structures for connecting the inflow conduit extension to the inflow conduit and the outflow conduit extension to the outflow conduit so that the third sealing surfaces abut and compress against the fourth sealing surfaces to define therebetween conduit/extension inflow and outflow sealing lines, wherein blood flowing across each of the conduit/extension inflow and outflow sealing lines only contacts the flexible tubular wall members of the conduits and the flexible blood conduits of the extensions.

19. The device of claim 18, further including a biasing member provided as part of each of the attachment structures connecting the inflow conduit extension to the inflow conduit and the outflow conduit extension to the outflow conduit, the biasing member positioned to apply an elastic force urging each pair of third and fourth sealing surfaces toward one another and maintain a consistent blood-tight seal at the conduit/extension inflow and outflow sealing lines.

20. The device of claim 19, wherein the attachment structures each include an extension coupling member connected to the circular end portion and a conduit coupling member connected to the conduit housing, wherein one of the extension coupling member or conduit coupling member has a pair of axially facing and relatively displaceable surfaces, and wherein the biasing members are axially elastic and placed in compression between the axially facing surfaces to apply the elastic force.

21. The device of claim 20, wherein the biasing members are wave washers.

22. The device of claim 20, wherein the extension coupling member and conduit coupling member include mating threads and are screwed together.

23. The device of claim 15, further including a prosthetic valve disposed within each of the inflow and outflow conduits and sutured to tie wall member so that blood flowing through either of the inflow or outflow conduits contacts only the flexible tubular wall member, the prosthetic valve, and the sutures.

24. The device of claim 23, further including a flexible external stent provided for each of the inflow and outflow conduits between the respective conduit housings and flexible wall members, the stent being sutured to the flexible wall members and to the prosthetic valve within the conduit to support the valve therein.

25. The device of claim 24, wherein the prosthetic valve is a trifoliate natural tissue valve, having three commissures, and wherein the external stent includes a metallic wireform having three axially-extending commissure supports aligned with each commissure of the natural tissue valve.

26. The device of claim 15, wherein the wall member is a fabric sheet material having an outer surface coated with a blood-impermeable biologically-compatible material and an inner porous surface to provide a site for growth of a biological interface.

27. A ventricular assist device for implantation in a human host, comprising:

a pump including a rigid housing and a flexible unitary liner within the housing defining a variable volume chamber;

inflow and outflow openings to the variable volume chamber defined by tubular co-extensions of the pump housing and inner unitary liner, each of the inflow and outflow openings terminating in a circular first sealing surface formed by the unitary liner;

inflow and outflow conduits attached, respectively, to the inflow and outflow openings of the pump, each conduit having opposed open ends and being adapted to channel blood between the variable volume chamber and a host circulatory system, each conduit having a rigid, generally tubular housing, a flexible tubular wall member within the conduit housing, and a circular second sealing surface on one end formed by the wall member and a circular third sealing surface on the opposite end from the second sealing surface and also formed by the wall member;

attachment structures for connecting the inflow conduit to the inflow opening and the outflow conduit to the outflow opening so that the first sealing surfaces abut and compress against the second sealing surfaces to define therebetween conduit/pump inflow and outflow sealing lines, wherein blood flowing from the inflow conduit across the conduit/pump inflow sealing line into the variable volume chamber and then across the conduit/pump outflow sealing line to the outflow conduit only contacts the flexible tubular wall members of the conduits and the unitary liner of the pump;

inflow and outflow flexible conduit extensions adapted to communicate blood between the host circulatory system and the inflow and outflow conduits, respectively, each extension comprising an inner flexible blood conduit coaxially disposed within an outer plastic sheath terminating in a rigid circular end portion, and including a circular fourth sealing surface formed by the flexible blood conduit; and attachment structures for connecting the inflow conduit extension to the inflow conduit and the outflow conduit extension to the outflow conduit so that the third sealing surfaces abut and compress against the fourth sealing surfaces to define therebetween conduit/extension inflow and outflow sealing lines, wherein blood flowing across each of the conduit/extension inflow and outflow sealing lines only contacts the flexible tubular wall members of the conduits and the flexible blood conduits of the extensions.

28. The device of claim 27, further including a prosthetic valve disposed within each of the inflow and outflow conduits and sutured to the wall member so that blood flowing through the device only contacts the flexible blood conduits, the flexible tubular wall members, the prosthetic valves, and the sutures.

29. The device of claim 28, further including a flexible external stent provided for each of the inflow and outflow conduits between the respective conduit housings and flexible wall members, the stent being sutured to the flexible wall members and to the prosthetic valve within the conduit to support the valve therein.

30. The device of claim 29, wherein the prosthetic valve is a trifoliate natural tissue valve, having three commissures, and wherein the external stent includes a metallic wireform having three axially-extending commissure supports aligned with each commissure of the natural tissue valve.

31. The device of claim 27, wherein the wall member is a fabric sheet material having an outer surface coated with a blood-impermeable biologically-compatible material and an inner porous surface to provide a site for growth of a biological interface.

32. A ventricular assist device for implantation in a human host, comprising:

a pump including a rigid housing and a flexible unitary liner within the housing defining a variable volume chamber;

inflow and outflow openings to the variable volume chamber defined by tubular co-extensions of the pump housing and inner unitary liner, each of the inflow and outflow openings terminating in a circular first sealing surface formed by the unitary liner;

inflow and outflow conduits attached, respectively, to the inflow and outflow openings of the pump, each conduit having opposed open ends and being adapted to channel blood between the variable volume chamber and a host circulatory system, each conduit having a rigid, generally tubular housing, a flexible tubular wall member within the conduit housing, a circular second sealing surface on one end formed by the wall member, and a circular third sealing surface on the opposite end from the second sealing surface, the third sealing surface formed by the wall member;

attachment structures for connecting the inflow conduit to the inflow opening and the outflow conduit to the outflow opening so that the first sealing surfaces abut and axially compress against the second sealing surfaces to define therebetween conduit/pump inflow and outflow sealing; lines, wherein blood flowing from the inflow conduit across the conduit/pump inflow sealing line into the variable volume chamber and then across the conduit/pump outflow sealing line to the outflow conduit only contacts the flexible tubular wall members of the conduits and the unitary liner of the pump;

a biasing member provided as part of each of the, attachment structures connecting the inflow conduit to the inflow opening and the outflow conduit to the outflow opening, the biasing member positioned to apply an elastic force urging each pair of first and second sealing surfaces toward one another and maintain a consistent blood-tight seal at the conduit/pump inflow and outflow sealing lines;

inflow and outflow flexible conduit extensions adapted to communicate blood between the host circulatory system and the inflow and outflow conduits, respectively, each extension comprising an inner flexible blood conduit coaxially disposed within an outer plastic sheath terminating in a rigid circular end portion, and including a circular fourth sealing surface formed by the flexible blood conduit; and attachment structures for connecting the inflow conduit extension to the inflow conduit and the outflow conduit extension to the outflow conduit so that the third sealing surfaces abut and compress against the fourth sealing surfaces to define therebetween conduit/extension inflow and outflow sealing lines, wherein blood flowing across each of the conduit/extension inflow and outflow sealing lines only contacts the flexible tubular wall members of the conduits and the flexible blood conduits of the extensions.

33. The device of claim 32, further including a biasing member provided as part of each of the attachment structures connecting the inflow conduit extension to the inflow conduit and the outflow conduit extension to the outflow conduit, the biasing member positioned to apply an elastic force urging each pair of third and fourth sealing surfaces toward one another and maintain a consistent blood-tight seal at the conduit/extension inflow and outflow sealing lines.

34. The device of claim 32, wherein the attachment structures each include an extension coupling member connected to the circular end portion and a conduit coupling member connected to the conduit housing, wherein one of the extension coupling member or conduit coupling member has a pair of axially facing and relatively displaceable surfaces, and wherein the biasing members are axially elastic and placed in compression between the axially facing surfaces to apply the elastic force.

35. The device of claim 34, wherein the biasing members are wave washers.

36. The device of claim 34, wherein the extension coupling member and conduit coupling member include mating threads and are screwed together.

37. The device of claim 32, wherein the wall member is a fabric sheet material having an outer surface coated with a blood-impermeable biologically-compatible material and an inner porous surface to provide a site for growth of a biological interface.

38. A ventricular assist device for implantation in a human host, comprising:

a pump including a rigid housing and a flexible unitary liner within the housing defining a variable volume chamber;

inflow and outflow openings to the variable volume chamber defined by tubular co-extensions of the pump housing and inner unitary liner, each of the inflow and outflow openings terminating in a circular first sealing surface formed by the unitary liner;

inflow and outflow conduits attached, respectively, to the inflow and outflow openings of the pump, each conduit having opposed open ends and being adapted to channel blood between the variable volume chamber and a host circulatory system, each conduit having a rigid, generally tubular housing, a flexible tubular wall member within the conduit housing, and a circular second sealing surface on one end formed by the wall member;

attachment structures for connecting the inflow conduit to the inflow opening and the outflow conduit to the outflow opening so that the first sealing surfaces abut and axially compress against the second sealing surfaces to define therebetween conduit/pump inflow and outflow sealing, lines, wherein blood flowing from the inflow conduit across the conduit/pump inflow sealing line into the variable volume chamber and then across the conduit/pump outflow sealing line to the outflow conduit only contacts the flexible tubular wall members of the conduits and the unitary liner of the pump;

a biasing member provided as part of each of the attachment structures connecting the inflow conduit to the inflow opening and the outflow conduit to the outflow opening, the biasing member positioned to apply an elastic force urging each pair of first and second sealing surfaces toward one another and maintain a consistent blood-tight seal at the conduit/pump inflow and outflow sealing lines;

a prosthetic valve disposed within each of the inflow and outflow conduits and sutured to the wall member so that blood flowing through either of the inflow or outflow conduits contacts only the flexible tubular wall member, the prosthetic valve, and the sutures; and a flexible external stent provided for each of the inflow and outflow conduits between the respective conduit housings and flexible wall members, the stent being sutured to the flexible wall members and to the prosthetic valve within the conduit to support the valve therein.

39. The device of claim 38, wherein the prosthetic valve is a trifoliate natural tissue valve, having three commissures, and wherein the external stent includes a metallic wireform having three axially-extending commissure supports aligned with each commissure of the natural tissue valve.

40. The device of claim 38, wherein the wall member is a fabric sheet material having an outer surface coated with a blood-impermeable biologically-compatible material and an inner porous surface to provide a site for growth of a biological interface.

* * * * *